(12) United States Patent
Mennen et al.

(10) Patent No.: US 9,061,972 B2
(45) Date of Patent: Jun. 23, 2015

(54) APPARATUS FOR THE DECOMPOSITION OF NON-CONVERTED AMMONIUM CARBAMATE IN UREA SOLUTIONS IN A UREA SYNTHESIS PROCESS

(75) Inventors: Johannes Henricus Mennen, Meijel (NL); Joseph Maria Gerardus Eijkenboom, Sittard (NL)

(73) Assignee: STAMICARBON, B.V., Sittard (NL)

( * ) Notice: Subject to any disclaimer, the term of this patent is extended or adjusted under 35 U.S.C. 154(b) by 595 days.

(21) Appl. No.: 13/390,723

(22) PCT Filed: Aug. 9, 2010

(86) PCT No.: PCT/EP2010/061555
§ 371 (c)(1),
(2), (4) Date: Mar. 30, 2012

(87) PCT Pub. No.: WO2011/020732
PCT Pub. Date: Feb. 24, 2011

(65) Prior Publication Data
US 2012/0282149 A1 Nov. 8, 2012

(30) Foreign Application Priority Data
Aug. 17, 2009 (EP) .................................... 09010564

(51) Int. Cl.
*B01J 19/24* (2006.01)
*C07C 273/04* (2006.01)
*B01J 10/00* (2006.01)
*B01J 19/00* (2006.01)

(52) U.S. Cl.
CPC .............. *C07C 273/04* (2013.01); *B01J 10/00* (2013.01); *B01J 19/0053* (2013.01); *B01J 19/2415* (2013.01); *B01J 2219/00081* (2013.01)

(58) Field of Classification Search
CPC .............. B01J 9/24; B01J 19/00; B01J 10/00; B01D 19/00; B01D 1/06; C01C 1/04; C01J 10/00
USPC ........................................................ 422/187
See application file for complete search history.

(56) References Cited

U.S. PATENT DOCUMENTS

| 4,134,939 | A | * | 1/1979 | Zardi et al. ................. 261/112.1 |
| 4,199,537 | A | | 4/1980 | Zardi et al. |
| 4,317,787 | A | * | 3/1982 | Lagana' ..................... 261/112.1 |
| 4,899,813 | A | * | 2/1990 | Menicatti et al. ............. 165/133 |
| 5,582,656 | A | | 12/1996 | Kangas et al. |
| 2005/0042042 | A1 | | 2/2005 | Clarke |
| 2008/0093064 | A1 | | 4/2008 | Gianazza |

FOREIGN PATENT DOCUMENTS

| CN | 101097125 A | 1/2008 |
| EP | 1195194 | 4/2002 |
| EP | 1491836 | 12/2004 |
| EP | 1688511 | 8/2006 |
| GB | 1188051 | 4/1970 |

* cited by examiner

*Primary Examiner* — Walter D Griffin
*Assistant Examiner* — Huy-Tram Nguyen
(74) *Attorney, Agent, or Firm* — Banner & Witcoff, Ltd.

(57) ABSTRACT

An apparatus used for the decomposition of non-converted ammonium carbamate in a supplied urea solution in a urea stripping synthesis section. The apparatus comprises a number of heat exchanger tubes between a top chamber and a bottom chamber, a liquid distributor mounted on each heat exchanger tube and a gas/liquid separator together with a perforated basket at the centre of the top chamber.

7 Claims, 3 Drawing Sheets

APPARATUS FOR THE DECOMPOSITION OF NON-CONVERTED AMMONIUM CARBAMATE IN UREA SOLUTIONS IN A UREA SYNTHESIS PROCESS

CROSS-REFERENCE TO RELATED APPLICATIONS

This application is a U.S. National Stage application under 35 U.S.C. §371 of International Application PCT/EP2010/061555 (published as WO 2011/020732 A1), filed Aug. 9, 2010, which claims priority to Application EP 09010564.4, filed Aug 17, 2009. Benefit of the filing date of each of these prior applications is hereby claimed. Each of these prior applications is hereby incorporated by reference in its entirety.

Urea can be prepared by introducing an ammonia excess together with carbon dioxide at a pressure between 12 and 40 MPa and at a temperature between 150 and 250° C. into a urea synthesis section. The resulting urea formation can be presented in the form of two consecutive reaction steps, in a first step ammonium carbamate being formed according to the exothermic reaction I:

$$2NH_3 + CO_2 \rightarrow H_2N-CO-ONH_4 \quad (I)$$

after which the ammonium carbamate formed is dehydrated in a second step to give urea according to the endothermic equilibrium reaction II:

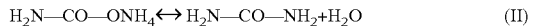

$$H_2N-CO-ONH_4 \leftrightarrow H_2N-CO-NH_2 + H_2O \quad (II)$$

The extent to which these reactions take place, depends among other things on the temperature and the ammonia excess used. The reaction product is obtained in the form of a urea solution comprises typically urea, water, unbound ammonia and ammonium carbamate. The ammonium carbamate and the ammonia are removed from the solution and are preferably returned to the urea synthesis section. In addition to the above-mentioned solution in the urea synthesis section, a gas mixture is formed which consists of unconverted ammonia and carbon dioxide together with inert gases, the so called reactor off-gas. The urea synthesis section may comprise separate zones for the formation of ammonium carbamate and urea. These zones may also be combined in a single apparatus.

A urea stripping plant is understood to be a urea plant in which the decomposition of ammonium carbamate that has not been converted into urea and the expulsion of the usual ammonia excess largely takes place at a pressure that is essentially almost equal to the pressure in the synthesis reactor. This decomposition and expulsion take place in one or more strippers installed downstream of the urea synthesis section, possibly with the aid of a stripping gas such as, for example, carbon dioxide and/or ammonia, and with the addition of heat. It is also possible to use a thermal stripper. Thermal stripping means that use is made exclusively of the supply of heat to decompose ammonium carbamate and to remove the ammonia and carbon dioxide from the urea solution. The gas stream leaving the thermal stripper containing ammonia and carbon dioxide is condensed in a high-pressure condenser and then returned to the urea synthesis section.

In a urea stripping plant the synthesis zone is operated at a temperature of 160-240° C. and preferably at a temperature of 170-220° C. The pressure in the synthesis reactor is 12-21 MPa, preferably 12.5-20 MPa. The ammonia to carbon dioxide molar ratio (N/C ratio) in the urea synthesis section of a stripping plant lies usually in between 2.2 and 5 and preferably between 2.5 and 4.5 mol/mol. The synthesis section can be a single reactor or a plurality of reactors arranged in parallel or series.

After stripping, the pressure of the stripped urea solution is reduced in the urea recovery and the urea solution is concentrated by the evaporation of water. The produced carbamate stream formed in a recovery section operating at a lower pressure than the pressure in the urea synthesis section, is preferably returned to the urea synthesis section. The recovery section can consist of a single section or a plurality of recovery sections arranged in series.

A frequently used method for the preparation of urea according to a stripping process is the Snamprogetti ammonia stripping process as for example described in U.S. Pat. No. 1,188,051 published on Apr. 15, 1970. In such a urea stripping process, the pressure difference between the reactor and the high-pressure stripper is usually in between 0.1 and 5 MPa and preferably between 0.5 and 0.2 MPa. A carbon dioxide feed in that method is usually completely added to the reactor. The carbon dioxide feed contains an inert vapor and often air is supplied to that carbon dioxide to keep the materials used in the synthesis resistant against excessive corrosion. The urea solution leaving the reactor containing urea, water and non-converted ammonium carbamate together with the inert vapor that contains non-converted ammonia and carbon dioxide gas are supplied after flashing to a high-pressure stripper. A high-pressure stripper is a heat exchanger comprising a shell and one or more tubes. From the shell, steam is supplied that provides the required heat necessary for the decomposition reaction of ammonium carbamate into ammonia and carbon dioxide vapor. At the top of the tubes, the urea solution is added and the liquid flows as a liquid film along the tube to the bottom channel of the stripper. The released vapor by the decomposition of the ammonium carbamate reaction leaves the heat exchanger tubes at the top. It is possible that stripping gas is added at the bottom of the heat exchanger tubes in order to improve the decomposition efficiency. It is also possible that air is supplied at the bottom of the heat exchanger to protect the material of the process side of the apparatus against excessive corrosion. Excessive corrosion is understood to be severely etching of the construction material.

The invention relates to an apparatus for the decomposition of ammonium carbamate in a urea synthesis section of a urea stripping plant comprising a number of heat exchanger tubes between a top chamber and a bottom chamber.

The applicant has found an apparatus, also called a high pressure stripper, that optimizes the liquid distribution over the heat exchanger tubes in order to improve the performance of the high-pressure stripper. State of the art high-pressure strippers often suffer from excessive corrosion of the heat exchanger tubes as well as a decrease in efficiency of the decomposition of ammonium carbamate. A decreased efficiency leads to an excessive amount of ammonium carbamate passing from the high-pressure stripper to the downstream recovery section(s) causing capacity limitations of the plant and/or excessive ammonia emissions.

This problem is solved by the apparatus of the present invention in that the top chamber comprises a gas/liquid separator. A gas/liquid separator in the top chamber of the high-pressure stripper separates the gas phase from the liquid phase before the liquid distribution over the heat exchanger tubes of the stripper takes place. The heat exchanger tubes are provided with a liquid distributor that enables to equally load every heat exchanger tube with urea solution Surprisingly, this results in the liquid to be equally distributed over the heat exchanger tubes of that stripper, thus avoiding excessive corrosion of those tubes and causing an optimal stripper efficiency.

In a preferred embodiment of the invention, the top chamber further comprises a perforated liquid distribution basket at the center of the top chamber of the apparatus.

By said perforated liquid distribution basked an even better distribution of the liquid over the heat exchanger tubes is obtained.

Preferably the gas/liquid separator is a tangential type or a cyclone type.

The gas/liquid separator and or the distribution basked can be made of several materials like stainless steel, titanium or zirconium bimetallic material. Preferably the material is a ferrite/austenite as for example described in U.S. Pat. No. 5,582,656.

The invention will be explained in greater detail below, using the drawings.

Figure 1:
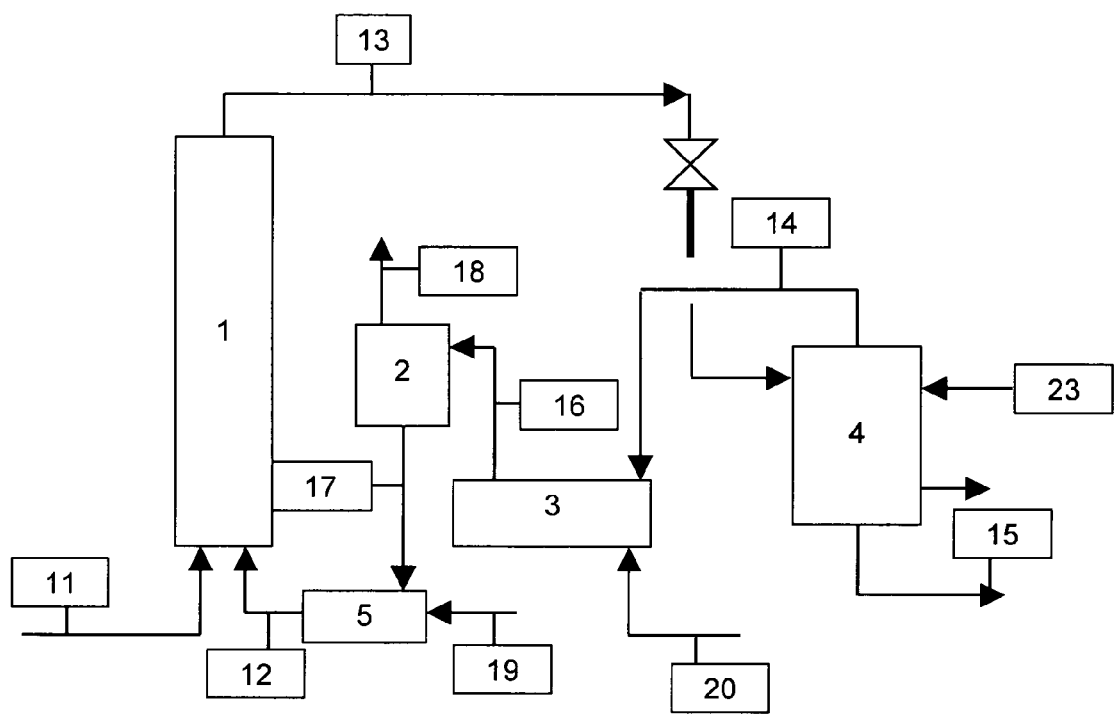
FIG. 1 is a schematic diagram describing a typical state of the art urea stripping process.

In FIG. 1 carbon dioxide is added to the reactor (1) in the urea synthesis section of the urea stripping process via (11). The carbon dioxide may contain an inert gas, typically air to prevent excessive corrosion. In the reactor (1) the hydration reaction from ammonium carbamate into urea takes place. The reaction is typically carried out at a pressure in between 14 MPa and 18 MPa, but other pressures are possible as well. The formed urea solution, having a temperature of 175° C. to 190° C., together with the inert vapor are sent to the stripper (4) via a two-phase line (13). In that line (13) usually a valve is installed to ensure a pressure difference of about 0.2 to 2 MPa between the reactor (1) and the stripper (4), allowing the urea solution to be flashed. In the stripper (4) the decomposition of non-converted ammonium carbamate takes place. A high-pressure stripper typically comprises a shell and tube type heat exchanger. Heat by means of saturated steam (23) with a pressure in between 1 MPa and 3 MPa is added to the shell side of that heat exchanger to provide the necessary heat for the decomposition reaction. The stripped urea solution leaves the synthesis zone to one or more downstream processing section(s) via the liquid line (15).

The vapor, leaving the stripper (4) via line (14) is sent to a carbamate condenser (3) in the urea synthesis section. Ammonium carbamate formed in the downstream recovery section(s) is re-introduced in the synthesis section through line (20) via the carbamate condenser (3). The heat released by the ammonium carbamate reaction (I) is usually used to generate steam that is used in the e.g. heaters and ejectors in the downstream processing sections of the urea stripping plant. The carbamate condenser (3) can be a falling-film type condenser, a kettle type condenser as well as a submerged type condenser.

The formed ammonium carbamate together with the non-converted ammonia and carbon dioxide gas, are sent via line (16) to a liquid/gas separator (2) in which the vapor phase is separated from the liquid phase. The vapor phase leaves the synthesis zone via line (18) and is typically sent to the downstream recovery section(s), that operate at a lower pressure than the synthesis section. The liquid phase, containing ammonium carbamate, water, dissolved ammonia and carbon dioxide and in some cases urea is sent via line (17) to a high-pressure ammonia ejector (5). The high-pressure ammonia ejector (5) increases the pressure of said liquid by about 0.2 to 2 MPa. As a driving force ammonia, introduces via (19) is used. The ammonia may be heated before it is used as driving force for the ejector (5). The formed ammonium carbamate together with the ammonia is sent via line (12) to the reactor (1) where the urea synthesis reaction takes place until it approaches the equilibrium described in reaction (II). The ammonia to carbon dioxide molar ratio in the synthesis zone is typically between 2.2 and 5 and more specifically between 2.5 and 4.

Figure 2:
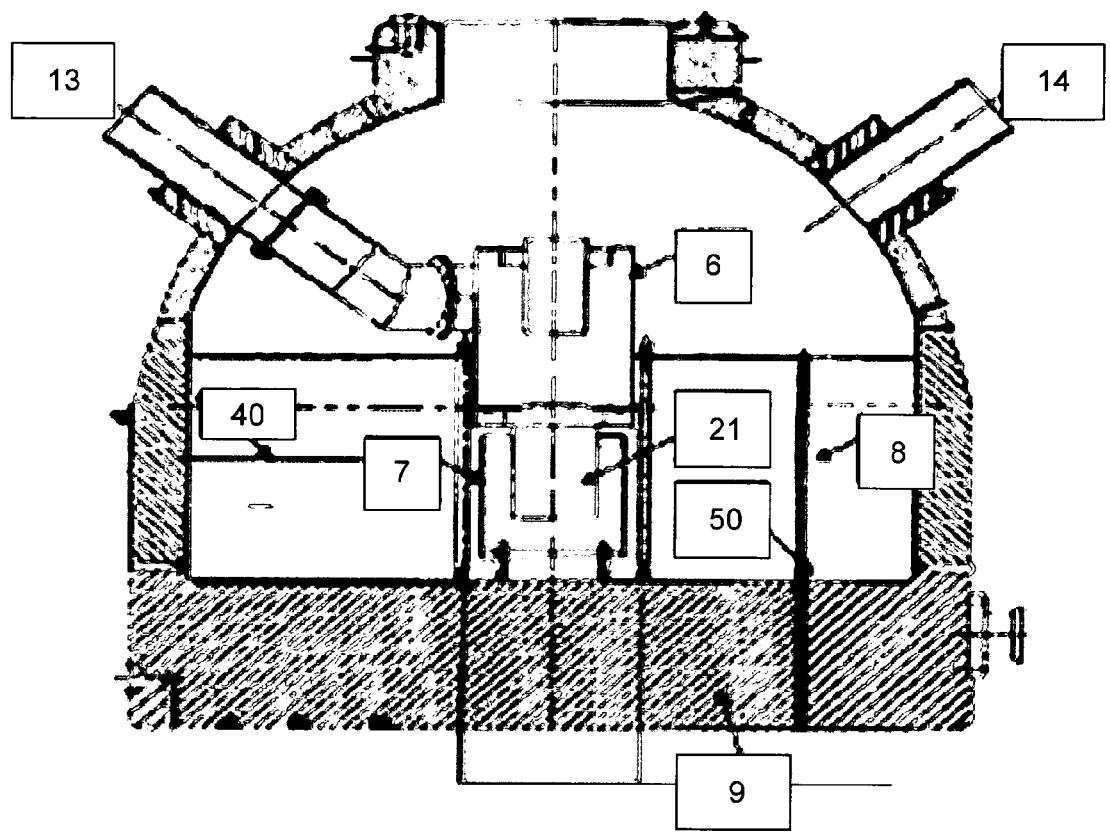
FIG. 2 shows an example of a liquid distribution over the heat exchanger tubes according the invention.

FIG. 2 shows an example of the top chamber of the apparatus according to the invention.

The mixture of gas and urea solution from the urea reactor (1) in the synthesis section enters the top channel of the reactor via a pipe (13) connected to a gas/liquid separator (6). This gas/liquid separator (6) is preferable a tangential type or a cyclone type. In the gas/liquid separator (6), the gas fraction is separated from the liquid fraction. The gas fraction leaves the gas/liquid separator at the top via pipe (14) that is connected to the upper part of the top chamber. The liquid fraction is discharged via (21) to the perforated liquid distribution basket (7) from where the liquid is distributed over the cross sectional diameter of the top chamber, thus creating a liquid level (40) above the liquid distributors (50). Via the liquid distributors (50) every heat exchanger tube (10) is loaded with urea solution equally. The vapor, released by the decomposition of ammonium carbamate in the urea solution, leaves the heat exchanger (10) tube via the gas tube (8) to the upper part of the top chamber. That vapor together with the gas from the gas/liquid separator (6) leaves the stripper via a nozzle (not shown) and pipe (14) to the processing part in the urea synthesis section.

Figure 3:
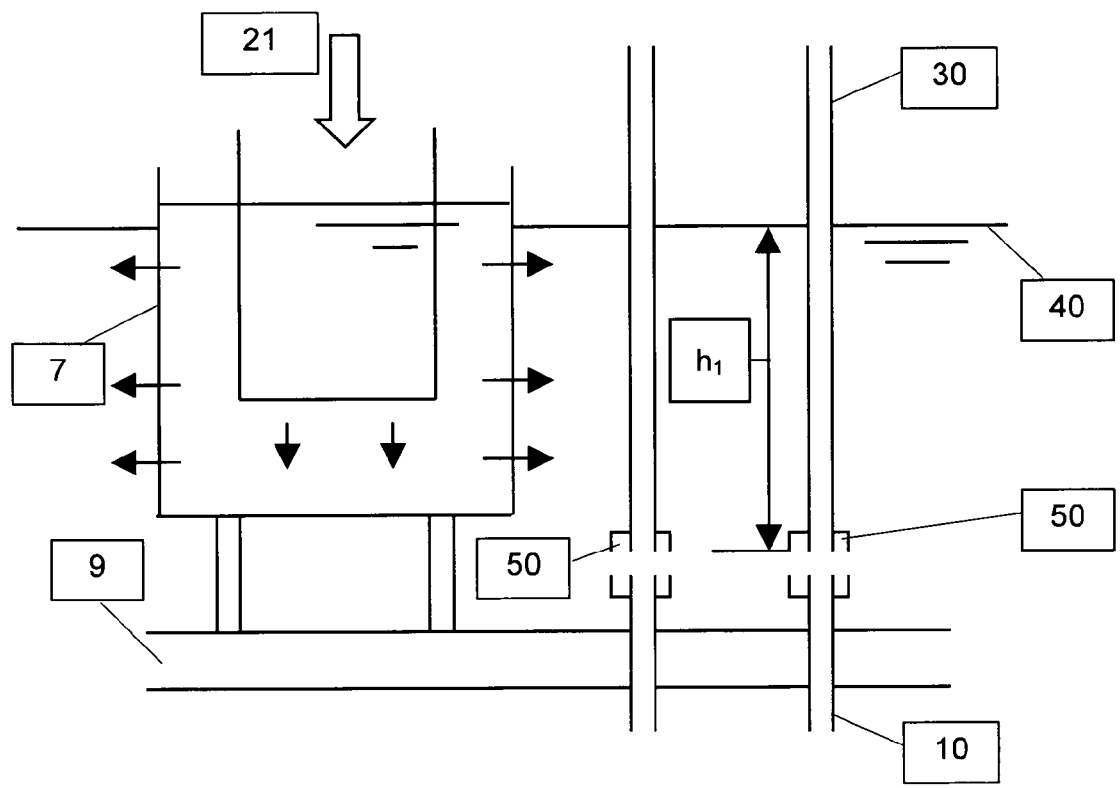
FIG. 3 shows an Example of the top channel of the apparatus according the invention.

FIG. 3 shows an example of an embodiment of the liquid distribution over the heat exchanger tubes according the invention.

Liquid (21) from gas/liquid separator enters the liquid distribution basket (7) which is located in the centre of the top chamber of the stripper. To ensure a steady liquid level above the tube sheet (9), the basket may be provided with a number of holes or may be consist of a frame with fine mesh gauze. The basket causes the liquid to be equally divided over the cross sectional area of the stripper top chamber. The stripping performance is optimal in case the liquid load on each heat exchanger tube is equal. According the invention this is realized by creating and assuring a constant liquid static head $h_1$ above the liquid distributor (50 for each heat exchanger tube (10). The difference between the static heads on each of the liquid distributors (50) over the cross sectional diameter of the top channel shall be less than 200 mm and preferable the difference is not more than 100 mm. To obtain an as small as possible difference between the static heads on the liquid distributors (50), the liquid distribution basket is perforated with 1 to 6 liquid holes and preferable 2 to 4 liquid holes. The diameter of the holes in the liquid distributor is 1 to 4 mm and preferable 2 to 3 mm.

The formed vapor in the heat exchanger tube (10), caused by the decomposition of ammonium carbamate into ammonia and carbon dioxide and if applicable an additional stripping gas, leaves the heat exchanger tube (10) via gas tube (30). The stripper is designed such that the liquid level at all circumstances is lower than the length of the gas tubes (8). This can be obtained by varying the size of the liquid distributors (50).

The invention claimed is:

1. An apparatus for the decomposition of ammonium carbamate in a urea synthesis section of a urea stripping plant comprising heat exchanger tubes between a top chamber and a bottom chamber characterized in that the top chamber comprises a gas/liquid separator and the heat exchanger tubes are provided with liquid distributors, the apparatus further comprising a perforated liquid distribution basket at the centre of the top chamber of the apparatus, wherein the heat exchanger tubes and liquid distributors are external to the liquid distribution basket.

2. An apparatus according to claim 1 characterized that the liquid distribution basket is perforated with holes with a diameter of 1-4 mm or the liquid distribution basket is fabricated in a frame of mesh gauze.

3. An apparatus according to claim 1 characterized that the gas/liquid separator, the distribution basket, or both are made of stainless steel, titanium or zirconium.

4. An apparatus according to claim 1, characterized that the gas/liquid separator is a tangential type or cyclone type.

5. The apparatus of claim 2, wherein the holes have a diameter of 2-3 mm or the basket is fabricated in a frame of mesh gauze.

6. The apparatus of claim 3, wherein the gas/liquid separator, the distribution basket, or both are made of a ferrite/austenite material.

7. An existing apparatus for the decomposition of ammonium carbamate in a urea synthesis section of a urea stripping plant comprising a number of heat exchanger tubes between a top chamber and a bottom chamber wherein the top chamber is modified such that the modified top chamber comprises a gas/liquid separator and the heat exchanger tubes are provided with liquid distributors the existing apparatus further comprising a perforated liquid distribution basket at the centre of the top chamber of the apparatus, wherein the heat exchanger tubes and liquid distributors are external to the liquid distribution basket.

* * * * *